United States Patent
De Saizieu et al.

(10) Patent No.: US 8,044,094 B2
(45) Date of Patent: Oct. 25, 2011

(54) AGENTS FOR PREVENTING AND TREATING DISORDERS CONNECTED TO IMPAIRED NEUROTRANSMISSION

(75) Inventors: Antoine De Saizieu, Brunstatt (FR); Ann Fowler, Rheinfelden (CH); Regina Goralczyk, Grenzach-Wyhlen (DE); Goede Schueler, Elmeldingen (DE); Bernd Mussler, Lahr (DE)

(73) Assignee: DSM IP Assets B.V., Heerlen (NL)

( * ) Notice: Subject to any disclaimer, the term of this patent is extended or adjusted under 35 U.S.C. 154(b) by 1120 days.

(21) Appl. No.: 11/665,072

(22) PCT Filed: Oct. 21, 2005

(86) PCT No.: PCT/CH2005/000621
§ 371 (c)(1),
(2), (4) Date: May 14, 2007

(87) PCT Pub. No.: WO2006/042441
PCT Pub. Date: Apr. 27, 2006

(65) Prior Publication Data
US 2007/0293563 A1  Dec. 20, 2007

(30) Foreign Application Priority Data

Oct. 22, 2004 (EP) .................................. 04025165

(51) Int. Cl.
*A61K 31/37* (2006.01)
(52) U.S. Cl. ......................................... 514/452; 514/457
(58) Field of Classification Search .................. 514/457, 514/452, 455; 549/282, 289
See application file for complete search history.

(56) References Cited

U.S. PATENT DOCUMENTS 3,707,474 A  12/1972  Razdan et al.
4,079,066 A  3/1978  Gardner

FOREIGN PATENT DOCUMENTS

WO  WO 2005/102316 A2  11/2005
WO  WO 2006 024545 A1  3/2006

OTHER PUBLICATIONS

Dobner et al., Helvetica Chimica Acta, 86(2003), 733-738.*
Stashenko et al., J. Biochem. Biophys. Methods, 43 (2000), 379-390.*
Wang et al., Zhongguo Yaoxue Zazhi, 1999, 34(3), 185-187 (Abstract).*
Um et al., Fitoterapia, 74 (2003), 638-642.*
Bairamian et al. (J. Essent. Oil Res., 16, 461-468 (Sep. 2004).*
Carotti et al, Bioorganic and Medicinal Chemistry Letter, vol. 12, p. 3551-3555 (2002).*
Gnerre et al, J. Med. Chem., vol. 43, p. 4747-4758 (2000).*
Takeuchi et al, Chem. Pharm. Bull., vol. 39(6), p. 1415-1421 (1991).*
Chen et al, Planta Med., vol. 61 p. 2-8 (1995).*
Yamada et al, "Spasmolytic Activity of Aurapten Analogs", Bioscience Biotechnology Biochemistry, Japan Soc. for Bioscience, Biotechnology and Agrochem, Tokyo, JP, vol. 61, No. 4, 1997, pp. 740-742.
Database Biosis, Biosciences Information Service, Philadelphia, PA, US; May 2000, Ogawa Kazunori et al, "Evaluation of auraptene content in citrus fruits and their products", XP 002377866 & Journal of Agricultural and Food Chemistry, vol. 48, No. 5, May 2000, pp. 1763-1769.
Database Biosis, Biosciences Information Service, Philadelphia, PA, US; 1992, Masuda Toshiya et al: "Coumarin constituents of the juice oil from citrus hassaku and their spasmolytic activity", XP002377867 & Bioscience Biotechnology and Biochemistry, vol. 56, No. 8, 1992, pp. 1257-1260.
Database Biosis, Biosciences Information Service, Philadelphia, PA, US; Sep. 28, 2001, Bocca Claudia et al, "Cytoskeleton-interacting activity of geiparvarin, diethylstillbestrol and conjugates", XP002377868 & Chemico-Biological Interactions, vol. 137, No. 3, Sep. 28, 2001, pp. 285-305.
Database FSTA, International Food Information Service (IFIS), Frankfurt-Main, DE; 2002, Takahashi Y et al, Rapid and convenient method for preparing aurapten-enriched product from hassaku peel oil: implications for cancer-preventive food additives, XP002377869 & Journal of Agricultural and Food Chemistry, vol. 50, No. 11, 2002, pp. 3193-3196.
Database WPI, XP002377874 & JP 04 128224 A, (Sankyo Co Ltd), Apr. 28, 1992.
International Search Report mailed May 17, 2006 in PCT/CH2005/000621.
Written Opinion mailed May 17, 2006 in PCT/CH2005/000621.

* cited by examiner

*Primary Examiner* — Bernard Dentz
(74) *Attorney, Agent, or Firm* — Nixon & Vanderhye P.C.

(57) ABSTRACT

The present invention refers to coumarin ethers of the formula (I), wherein $R^1$ is H, OH or (E)-3-methyl-but-2-enyl, $R^2$ is selected from the group consisting of methyl, 3-(4,5-dihydro-5,5-dimethyl-4-furanon-2-yl)-2-(E/Z)-butenyl, (E/Z)-3,7-dimethylocta-2,6-dienyl, 7-hydroxy-3,7-dimethyl-2-octen-6-on-yl and (E/Z,E/Z)-11-acetyl-oxy-3,7,11,11-tetramethyl-undeca-2,7-dien-10-on-yl, $R^3$ is H, $R^1$ and $R^2O$ together for the group —O—C(C(=$CH_2$)$CH_3$)H—$CH_2$—O— or the group —C(H)=C(H)—C($CH_3$)$_2$—O— or $R^2O$ and $R^3$ together form the group —O—C(H)(C($CH_3$)$_2$(H)—O—C(O)$CH_3$)—$CH_2$—, preferably to obliquin, for use as medicaments, especially for the treatment and/or prevention of disorders connected to impaired neurotransmission, as well as to dietary and pharmaceutical compositions and plant extracts containing such coumarin ethers and their uses.

5 Claims, 1 Drawing Sheet

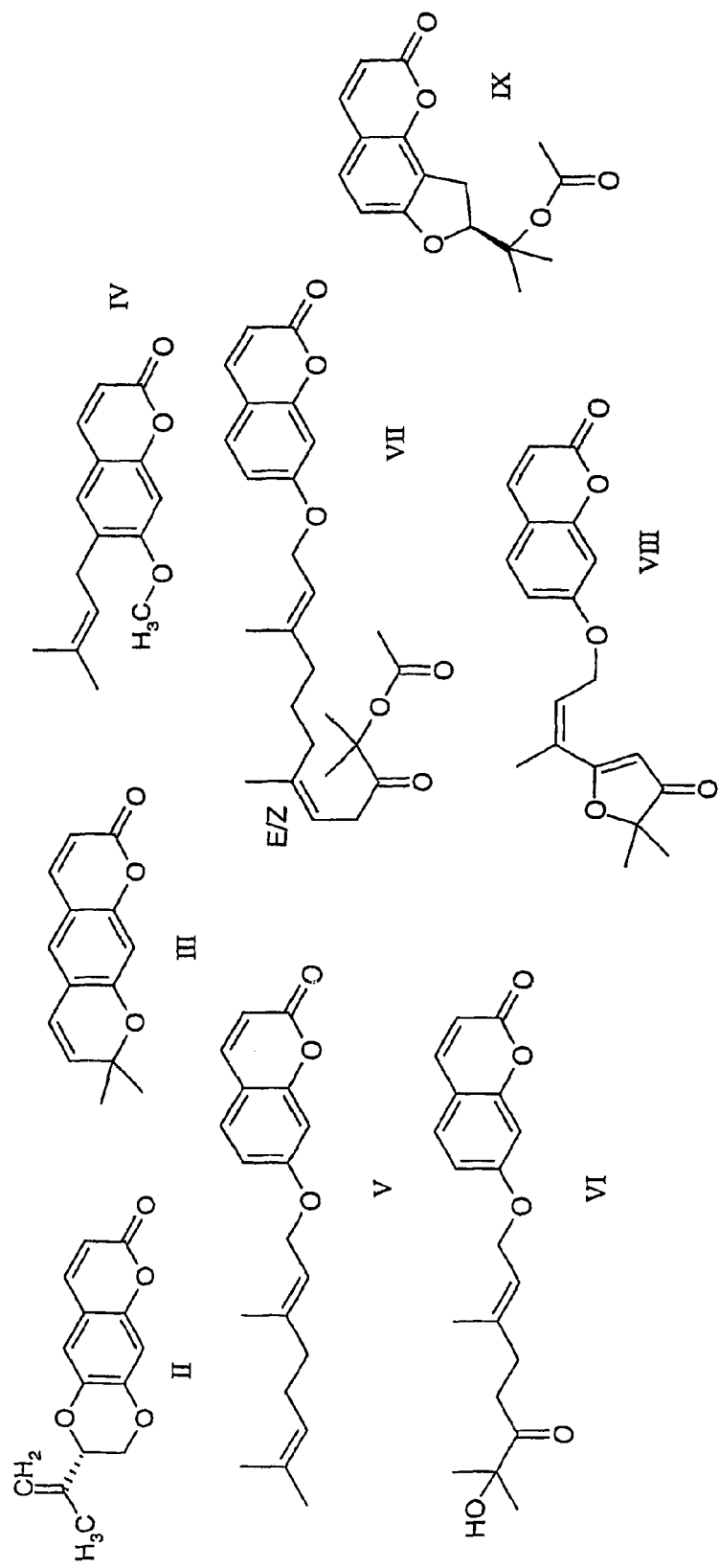
Fig. 1: Compounds of the formulae II to X

AGENTS FOR PREVENTING AND TREATING DISORDERS CONNECTED TO IMPAIRED NEUROTRANSMISSION

This application is the US national phase of international application PCT/CH2005/000621 filed 21 Oct. 2005 which designated the U.S. and claims benefit of EP 04025165.4, dated 22 Oct. 2004, the entire content of which is hereby incorporated by reference.

The present invention refers to coumarin ethers for use as medicaments, especially for the treatment of disorders connected to impaired neurotransmission, as well as to dietary and pharmaceutical compositions and plant materials and extracts containing such coumarin ethers and their uses.

It is well known that impaired neurotransmission, e.g. low neurotransmitter levels, is connected to mental diseases such as depression.

Compounds that increase neurotransmitter levels in the brain and thus enhance their transmission, exhibit therefore antidepressant properties as well as beneficial effects on a variety of other mental disorders ("Neurotransmitters, drugs and brain function" R. A. Webster (ed), John Wiley & Sons, New York, 2001, p. 187-211, 289-452, 477-498). The main neurotransmitters are serotonin, dopamine, noradrenaline (=norepinephrine), acetylcholine, glutamate, gamma-aminobutyric acid, as well as neuropeptides. Increase in neurotransmission is achieved by increasing the concentration of the neurotransmitter in the synaptic cleft thus making it available for increased or prolonged neurotransmission through inhibition of re-uptake into the pre-synaptic nerve end, or by preventing neurotransmitter catabolism by inhibition of degrading enzymes such as monoaminooxidase A and B.

Tricyclic antidepressant compounds (TCAs) such as imipramine, amitriptyline, and clomipramine e.g. inhibit the re-uptake of serotonin and noradrenaline. They are widely regarded as among the most effective antidepressants available, but they have a number of disadvantages because they interact with a number of brain receptors, e.g. with cholinergic receptors. Most importantly, TCAs are not safe when taken in overdose, frequently showing acute cardiotoxicity.

Another class of antidepressant drugs are the so-called SSRIs (selective serotonin re-uptake inhibitors) including fluoxetine, paroxetine, sertraline, citalopram, fluvoxamine that block the serotonin transporter (SERT), a high affinity sodium chloride-dependent neurotransmitter transporter that terminates serotonergic neurotransmission by uptake of serotonin. They have been proven as effective in the treatment of depression and anxiety, and are usually better tolerated than TCAs. These medications are typically started at low dosages and may be increased until they reach a therapeutic level. A common side effect is nausea. Other possible side effects include decreased appetite, dry mouth, sweating, infection, constipation, yawn, tremor, sleepiness and sexual dysfunction.

In addition, compounds that prevent the catabolism of neurotransmitters more broadly by inhibiting the monoaminooxidases (MAOs) A and B exhibit antidepressant effects. MAOs catalyse the oxidation of amino group containing neurotransmitters such as serotonin, noradrenaline, and dopamine.

Furthermore, modulators of neurotransmission exert pleiotropic effects on mental and cognitive functions.

There is a need for compounds for the treatment or prevention of mental diseases and/or disorders which do not show the negative side effects of known antidepressants. Many patients are interested in alternative therapies which could minimize the side effects associated with high-dose of drugs and yield additive clinical benefits. Severe depression is a long lasting and recurring disease, which is usually poorly diagnosed. Furthermore many patients suffer from mild or middle severe depression. Thus, there is an increasing interest in the development of compounds as well as pharmaceutical and/or dietary compositions that may be used to treat mental diseases/disorders or to prevent the development of mental diseases/disorders such as depression in people at risk, and to stabilize mood.

According to the present invention this demand is met with coumarin ethers of the formula I,

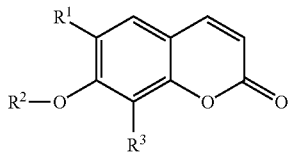

wherein $R^1$ is H, OH or (E)-3-methyl-but-2-enyl, $R^2$ is selected from the group consisting of methyl, 3-(4,5-dihydro-5,5-dimethyl-4-furanon-2-yl)-2-(E/Z)-butenyl, (E/Z)-3,7-dimethylocta-2,6-dienyl, 7-hydroxy-3,7-dimethyl-2-octen-6-on-yl and (E/Z,E/Z)-11-acetyloxy-3,7,11,11-tetramethyl-undeca-2,7-dien-10-on-yl, $R^3$ is H, $R^1$ and $R^2O$ together form the group —C(C(=CH$_2$)CH$_3$)H—CH$_2$—O— or the group —C(C)=C(H)—C(CH$_3$)$_2$O— or $R^2O$ and $R^3$ together form the group —O—C(H)(C(CH$_3$)$_2$(H))—O—(O)CH$_3$—CH$_2$—.

Thus, in one aspect the invention relates to a coumarin ether of the formula I with the definitions of $R^1$, $R^2$ and $R^3$ as given above, preferably to the coumarin ether wherein $R^1$ and $R^2O$ together form the group —O—C(C(=CH$_2$)CH$_3$)H—CH$_2$—O—, more preferably to obliquin, most preferably to (S)-obliquin, for use as medicament, particularly for use as medicament for the treatment of a disorder connected to impaired neurotransmission.

In another aspect, the invention relates to the use of a coumarin ether of the formula I as defined above for the manufacture of a composition for the treatment of a disorder connected to impaired neurotransmission, particularly for the manufacture of an antidepressant, a mood improver, a stress reliever, a condition improver, a reducer of anxiety and/or a reducer of obsessive-compulsive behaviour.

In still another aspect, the invention relates to a dietary composition containing at least one coumarin ether of the formula I as defined above as well as to a pharmaceutical composition containing at least one coumarin ether of the formula I as defined above and a conventional pharmaceutical carrier.

Further, the invention relates to a method for the treatment of a disorder connected to impaired neurotransmission in animals including humans, said method comprising administering an effective dose of a coumarin ether of the formula I as defined above to animals including humans which are in need thereof.

Animals in the context of the present invention include humans and encompass mammals, fish and birds. Preferred "animals" are humans, pet animals and farm animals.

Examples for pet animals are dogs, cats, birds, toy fish, guinea pigs, (jack) rabbits, hares and ferrets. Examples for farm animals are fish, pigs, horses, ruminants (cattle, sheep and goat) and poultry.

BRIEF DESCRIPTION OF THE DRAWING

In a preferred aspect of the present invention the coumarin ether of the formula I is selected from the group consisting of obliquin (compound of the formula II; see FIG. 1), xanthyletin (compound of the formula III; see FIG. 1), suberosin (compound of the formula IV; see FIG. 1), 7-geranyloxycoumarin (compound of the formula V; see FIG. 1), 6'-dehydromarmin (compound of the formula VI; see FIG. 1), geiparvarin (compound of the formula VIII; see FIG. 1), O-acetylcolumbianetin (compound of the formula IX; see FIG. 1) and the compound of the formula VII (see FIG. 1). More preferably the coumarin ether of the formula I is obliquin, most preferably the coumarin ether of the formula I is (S)-obliquin.

The term "coumarin ether of the formula I" also encompasses any material or extract of a plant containing such a coumarin ether of the formula I, especially any material or extract of a plant containing at least 90 weight-% of such a coumarin ether of the formula I based on the total weight of the plant material or extract. The terms "material of a plant" and "plant material" used in the context of the present invention mean any part of a plant.

"Obliquin" means the racemic mixture as well as pure R-obliquin or pure S-obliquin or any mixture of them. Obliquin can be isolated from plants like, but not limited to, *Cedrelopsis grevei, Ptaeroxylon obliquum, Lentopodium alpinum, Helichrysum* ssp., *Ifloga spicata, Nidorella anomala, Cneorum tricoccum, Phaenocoma prolifera* and *Cedrelopsis microfoliata* (Journal of Natural Products 2002, 65, 1349-1352).

Therefore, any material or extract of these plants or any other plant material or extract containing obliquin is also encompassed by this expression. "Obliquin" means both "natural" (isolated) and "synthetic" (manufactured) obliquin.

Obliquin's synthesis is described in J. Chem. Soc. (C) 1969, 526-531, as well as in Phytochemistry 1973, 12, 726-727.

7-Geranyloxycoumarin, also called "aurapten", can be isolated from plants like the following, but not limited to *Citrus* ssp., *Aegle marmelos, Poncirus trifoliata, Afraegle paniculata, Severinia buxifolia, Atalantia monophylla, Ptelea trifoliata* and *Fortunella hindsii*.

Therefore, any material or extract of these plants or any other plant material or extract containing 7-geranyloxycoumarin is also encompassed by this expression. "7-Geranyloxycoumarin" means both "natural" (isolated) and "synthetic" (manufactured) 7-geranyloxycoumarin.

7-Geranyloxycoumarin can be prepared according to Tetrahedron Letters, 28(23), 2579-82; 1987.

Suberosin can be isolated from plants like the following, but not limited to *Plumbago zeylanica, Seseli* ssp., *Heracleum candicans, Citrus* ssp., *Prangos lipskyi* and *Prangos lophoptera*. Therefore, any material or extract of these plants or any other plant material or extract containing suberosin is also encompassed by this expression. "Suberosin" means both "natural" (isolated) and "synthetic" (manufactured) suberosin.

Suberosin's synthesis is described in several articles, i.e. in Journal of the Chemical Society, Chemical Communications 1986, 16, 1264-1266.

The compound of formula VII (CAS [374702-57-5]) can be isolated from *Ferula tadshikorum* and other plants. Therefore, any material or extract of these plants or any other plant material or extract containing the compound of formula VII is also encompassed by this expression. "Compound of formula VII" means both "natural" (isolated) and "synthetic" (manufactured).

6'-Dehydromamin can be isolated from the fruit of *Geijera parviflora* and other plants. Therefore, any material or extract of these plants or any other plant material or extract containing 6'-dehydromarmin is also encompassed by this expression. "6'-Dehydromarmin" means both "natural" (isolated) and "synthetic" (manufactured) 6'-dehydromarmin.

Geiparvarin can be isolated from the leaves of *Geijera panriflora* and other plants. Therefore, any material or extract of these plants or any other plant material or extract containing geiparvarin is also encompassed by this expression. "Geiparvarin" means both "natural" (isolated) and "synthetic" (manufactured) geiparvarin.

Geiparvarin can be prepared according to the process described in Journal of Organic Chemistry 1985, 50(21), 3997-4005 or in Bioorganic & Medicinal Chemistry Letters 2002, 12(24), 3551-3555.

(S)—O-Acetylcolumbianetin can be isolated from plants like, but not limited to *Cnidium monnieri* and *Angelica* ssp. Therefore, any material or extract of these plants is also encompassed by this expression. "O-Acetylcolumbianetin" means both "natural" (isolated) and "synthetic" (manufactured) O-acetylcolumbianetin.

Beside the (pure) compounds obliquin, xanthyletin, 7-geranyloxycoumarin, suberosin, 6'-dehydromarmin, geiparvarin, O-acetylcolumbianetin and the compound of the formula VII especially preferred are plant materials and plant extracts containing at least 90 weight-% of these compounds based on the total weight of the plant material/extract.

According to the present invention not only the coumarin ethers of formula I themselves, with the definitions of $R^1$, $R^2$ and $R^3$ and the preferences as given above, but also plant materials and extracts containing them, as well as dietary and pharmaceutical compositions containing them can be used as medicament, especially for the treatment of a disorder connected to impaired neurotransmission.

The dietary compositions according to the present invention may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellyfying agents, gel forming agents, antioxidants and antimicrobials.

The term "dietary compositions" comprises any type of nutrition such as (fortified) food/feed and beverages including also clinical nutrition, and also dietary supplements.

Beside a pharmaceutically acceptable carrier and at least one coumarin ether of the formula I with the definitions of $R^1$, $R^2$ and $R^3$ and the preferences as given above, the pharmaceutical compositions according to the present invention may further contain conventional pharmaceutical additives and adjuvants, excipients or diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like. The carrier material can be organic or inorganic inert carrier material suitable for oral/parenteral/injectable administration.

The dietary and pharmaceutical compositions according to the present invention may be in any galenic form that is suitable for administrating to the animal body including the human body, especially in any form that is conventional for oral administration, e.g. in solid form such as (additives/supplements for) food or feed, food or feed premix, fortified food or feed, tablets, pills, granules, dragées, capsules, and effervescent formulations such as powders and tablets, or in liquid form such as solutions, emulsions or suspensions as e.g. beverages, pastes and oily suspensions. The pastes may be filled into hard or soft shell capsules, whereby the capsules feature e.g. a matrix of (fish, swine, poultry, cow) gelatin, plant proteins or ligninsulfonate. Examples for other application forms are forms for transdermal, parenteral or injectable administration. The dietary and pharmaceutical compositions may be in the form of controlled (delayed) release formulations.

Examples of food are dairy products such as yoghurts.

Examples of fortified food are cereal bars, bakery items such as cakes and cookies.

Beverages encompass non-alcoholic and alcoholic drinks as well as liquid preparations to be added to drinking water and liquid food. Non-alcoholic drinks are e.g. soft drinks, sport drinks, fruit juices, lemonades, teas and milk based drinks. Liquid food are e.g. soups and dairy products (e.g. muesli drinks).

The coumarin ethers of formula I with the definitions of $R^1$, $R^2$ and $R^3$ and the preferences as given above can be used for the manufacture of medicaments for the treatment of a disorder connected to impaired neurotransmission.

In the context of this invention "treatment" also encompasses co-treatment as well as prevention. "Prevention" can be the prevention of the first occurrence (primary prevention) or the prevention of a reoccurrence (secondary prevention).

Thus, the present invention is also directed to a method for the prevention of a disorder connected to impaired neurotransmission in animals including humans, said method comprising administering an effective dose of a coumarin ether of the formula I with the definitions of $R^1$, $R^2$ and $R^3$ and the preferences as given above to animals including humans which are in need thereof. In this regard an effective dose of a coumarin ether of the formula I with the definitions of $R^1$, $R^2$ and $R^3$ and the preferences as given above may especially be used for maintaining the mental well-being, for maintaining a balanced cognitive function, for helping to reduce the risk of mood swings, for helping to retain a positive mood and for supporting cognitive wellness.

In the context of this invention the term "disorder" also encompasses diseases.

Medicaments for the treatment of disorders connected to impaired neurotransmission encompass antidepressants, mood improvers, stress relievers, condition improvers, anxiety reducers and obsessive-compulsive behaviour reducers. They all improve, enhance and support the physiological neurotransmission, especially in the central nervous system, and therefore alleviate mental malfunction.

Antidepressants are medicaments for treating mental, behavioral and emotional/affective, neurotic, neurodegenerative, eating and stress related disorders such as e.g. unipolar depression, bipolar depression, acute depression, chronic depression, subtonic depression, dysthymia, postpartum depression, premenstrual dysphoria/syndrom (PMS), climacteric depressive symptoms, aggression, attention deficit disorders (ADS), social anxiety disorders, seasonal affective disorders, anxiety (disorders), fibromyalgia syndrome, chronic fatigue, sleep disorders (insomnia), post-traumatic stress disorders, panic disorders, obsessive compulsive disorders, restless leg syndrome, nervousness, migraine/primary headaches and pain in general, emesis, bulimia, anorexia nervosa, binge eating disorder, gastrointestinal disorders, burn out syndrome, irritability and tiredness.

Antidepressants can also be used for (the manufacture of compositions for) primary and secondary prevention and/or the treatment of neurocognitive impairment. Furthermore they are also effective in the treatment of depressive symptoms or other symptoms related to disturbed neurotransmission occurring as comorbidity in chronic diseases such as cardiovascular diseases, strokes, cancer, Alzheimer disease, Parkinson disease, and others.

The coumarin ethers of the formula I with the definitions of $R^1$, $R^2$ and $R^3$ and the preferences as given above as well as plant materials and plant extracts (essentially) containing them and dietary/pharmaceutical compositions containing them are thus suitable for the treatment of animals including humans.

Especially pet animals and farm animals can be in conditions in need of enhanced or improved neurotransmission. Such conditions e.g. occur after capture or transport or with housing, when the animals develop analogous disorders and are distressed or aggressive, or display stereotypic behaviour, or anxiety and obsessive-compulsive behaviour.

Thus, the coumarin ethers of the formula I with the definitions of $R^1$, $R^2$ and $R^3$ and the preferences as given above can be used in general as antidepressants for animals including humans, preferably for humans, pet animals and farm animals.

In a further embodiment of the present invention the coumarin ethers of the formula I with the definitions of $R^1$, $R^2$ and $R^3$ and the preferences as given above find use as mood improver in general as well as for the manufacture of compositions for such use (plant materials/extracts; dietary/pharmaceutical compositions). "Mood improver" or "emotional wellness booster" means that the mood of a person treated with it is enhanced, that the self esteem is increased and/or that negative thoughts and/or negative tension are/is reduced. It also means the emotions are balanced and/or that the general, especially the mental, well being is improved or maintained, as well as that the risk of mood swings is (helped to be) reduced and that the positive mood is (helped to be) retained.

Moreover, coumarin ethers of the formula I with the definitions of $R^1$, $R^2$ and $R^3$ and the preferences as given above as well as compositions comprising an effective dose of them are useful for the treatment, prevention and the alleviation of stress related symptoms, for the treatment, prevention and alleviation of symptoms related to working overload, exhaustion and/or burn out, for the increase of the resistance or tolerance to stress and/or to favor and facilitate the relaxation in normal healthy individuals i.e. such compositions have an effect as "stress reliever".

Furthermore, coumarin ethers of the formula I with the definitions of $R^1$, $R^2$ and $R^3$ and the preferences as given above as well as compositions comprising an effective dose of them are useful for the treatment, prevention and alleviation of anxiety and obsessive-compulsive behaviour in humans and animals.

A further embodiment of the present invention relates to the use of coumarin ethers of the formula I with the definitions of $R^1$, $R^2$ and $R^3$ and the preferences as given above and to the use of compositions containing them (plant extracts; dietary/pharmaceutical compositions) as "condition improver", i.e. as means to reduce irritability and tiredness, to reduce or prevent or alleviate physical and mental fatigue, to favour undisturbed sleep, that is to act against insomnia and sleep disorders and to improve sleep, and to increase energy in more general terms, especially to increase the brain energy production, in diseased or normal healthy individuals. Moreover for cognition improvement in general, and especially for maintenance or improvement of attention and concentration, of the memory and of the capacity for remembering, of the learning ability, of the language processing, of problem solving and of intellectual functioning; for improvement of the short-term memory; for increasing the mental alertness; for enhancing the mental vigilance; for reducing the mental fatigue; for supporting cognitive wellness, for maintaining balanced cognitive function, for the regulation of hunger and satiety as well as for the regulation of motor activity.

The present invention not only refers to coumarin ethers of the formula I with the definitions of $R^1$, $R^2$ and $R^3$ and the preferences as given above and their compositions (i.e. plant extracts essentially containing them; dietary/pharmaceutical compositions containing them) for use as medicaments, especially for the treatment of disorders connected to impaired neurotransmission, but also for the methods for the treatment of such disorders themselves, as already mentioned above.

In an especially preferred embodiment of such method pet animals or farm animals whose disorders are associated with housing, capture or transport are treated and which may appear in form of anxiety or obsessive-compulsive behaviour.

For humans a suitable daily dosage of a coumarin ether of the formula I, with the definition for $R^1$, $R^2$ and $R^3$ and the preferences as given above, for the purposes of the present invention may be within the range from 0.001 mg per kg body weight to about 20 mg per kg body weight per day. More preferred is a daily dosage of about 0.01 to about 10 mg per kg body weight, and especially preferred is a daily dosage of about 0.05 to 5.0 mg per kg body weight. The amount of a plant material or plant extract containing such coumarin ether of the formula I can be calculated accordingly.

In solid dosage unit preparations for humans, the coumarin ether of the formula I, with the definition for $R^1$, $R^2$ and $R^3$ and the preferences as given above, is suitably present in an amount from about 0.1 mg to about 1000 mg, preferably from about 1 mg to about 500 mg per dosage unit.

In dietary compositions, especially in food and beverages for humans, the coumarin ether of the formula I, with the definition for $R^1$, $R^2$ and $R^3$ and the preferences as given above, is suitably present in an amount of from about 0.0001 (1 mg/kg) to about 5 weight-% (50 g/kg), preferably from about 0.001% (10 mg/kg) to about 1 weight-%, (10 g/kg) more preferably from about 0.01 (100 mg/kg) to about 0.5 weight-% (5 g/kg), based upon the total weight of the food or beverage.

In food and drinks in a preferred embodiment of the invention the amount of the coumarin ether of the formula I with the definitions of $R^1$, $R^2$ and $R^3$ and the preferences as given above is 10 to 30 mg per serving, i.e. 120 mg per kg food or drink.

For animals excluding humans a suitable daily dosage of a coumarin ether of the formula I, with the definition for $R^1$, $R^2$ and $R^3$ and the preferences as given above, for the purposes of the present invention may be within the range from 0.001 mg per kg body weight to about 1000 mg per kg body weight per day. More preferred is a daily dosage of about 0.1 mg to about 500 mg per kg body weight, and especially preferred is a daily dosage of about 1 mg to 100 mg per kg body weight.

The invention is illustrated further by the following examples.

EXAMPLES

In example 1 a racemic mixture of obliquin obtained from MicroSource Discovery Systems Inc, 21 George Washington Plaza, Gaylordsville, Conn. 06755 USA was used. It had a purity of ≧96%. In examples 2 and 3 a racemic mixture of obliquin synthesized according to J. Chem. Soc. (C) 1969, 526-531 was used. Xanthyletin were obtained from Microsource as well. 7-geranyloxycoumarin, 6'-dehydromarmin, geiparvarin, (S)—O-acetylcolumbianetin and suberosin were obtained from APIN Chemicals, 43d Milton Park, Abingdon, Oxon, OX14 4RU, United Kingdom. And the compound of the formula VII was obtained from InterBioScreen Ltd., Institutsky Prospect, 7a 142432 Chernogolovka, Russia.

Example 1

Serotonin Uptake Inhibition and Labeled Citalopram Displacement by Coumarin Ethers of the Formula I HEK-293 cells stably expressing the human serotonin reuptake transporter (hSERT) were obtained from R. Blakely, Vanderbilt University, USA. The cells were routinely grown in Dulbeco's Modified Eagles Medium, purchased from Bioconcept, Allschwil, Switzerland containing 10% fetal calf serum, penicillin, streptomycin, L-glutamine and the antibiotic G418 and passaged by trypsinisation. 1 day prior to the assay cells were seeded in the above mentioned medium. Immediately prior to the assay the medium was replaced by Krebs Ringers bicarbonate buffer, purchased from Sigma Chemicals Ltd., supplemented with 35 µM pargyline, 2.2 mM $CaCl_2$, 1 mM ascorbic acid and 5 mM N-2-hydroxyethylpiperazine-N'-2-ethanesulfonic acid (buffer called "Hepes"). Serotonin uptake into the cells was determined by addition of radio-labeled (3H) serotonin (Amersham Biosciences GE Healthcare, Slough, UK) to a concentration of 20 nM, and incubation for 30 minutes at room temperature. Following removal of unincorporated label by gentle washing three times with the above buffer, incorporated serotonin was quantified by liquid scintillation counting.

Membranes containing hSERT were prepared from the above cell line according to Galli et al, Journal of Experimental Biology 1995, 198, 2197-2212. 3 µg of membrane protein and 0.8 mg of wheat germ aglutinin coated SPA® (scintillation proximity assay) beads (Amersham Biosciences GE Healthcare, Slough, UK) per data point were mixed with radio-labeled (3H) citalopram (Amersham Biosciences GE Healthcare, Slough, UK) until a final concentration of 3.3 nM in 50 mM Tris-HCl, 300 mM NaCl (pH 7.4). After incubation for 18 hours at room temperature, the bound citalopram was quantified by liquid scintillation counting.

The effect of the coumarin ethers of formula I on the serotonin uptake and the citalopram binding was determined by its inclusion in the assay at a range of concentrations between 0.03 and 100 µM for 10 minutes prior to and during the addition of (3H) serotonin/citalopram. Serotonin uptake via the transporter and citalopram binding were both inhibited by the coumarin ethers of formula I in a dose dependent manner. The calculated inhibition constants $K_i$, derived from the measured IC50 using the Cheng—Prusoff equation (Y. C. Cheng, W. H. Prusoff, Biochem. Pharmacol. 1973, 22, p. 3099-3108), for inhibition of serotonin uptake and citalopram binding by coumarin ethers of the formula I are shown in Table 1.

TABLE 1

Inhibition constants for inhibition of serotonin uptake into transfected HEK-293 cells and displacement of labeled citalopram from hSERT containing membranes by coumarin ethers of formula I.

| Substance | Inhibition constant $K_i$ [µM] for tritiated serotonin uptake | Inhibition constant $K_i$ [µM] for tritiated citalopram displacement |
|---|---|---|
| Obliquin | 4.9 | 6.1 |
| Xanthyletin | 20.2 | 11.9 |
| Suberosin | 9.8 | 39.3 |

TABLE 1-continued

Inhibition constants for inhibition of serotonin uptake into transfected HEK-293 cells and displacement of labeled citalopram from hSERT containing membranes by coumarin ethers of formula I.

| Substance | Inhibition constant $K_i$ [μM] for tritiated serotonin uptake | Inhibition constant $K_i$ [μM] for tritiated citalopram displacement |
|---|---|---|
| 7-Geranyloxycoumarin | 22.4 | 24.2 |
| Compound of the formula VII | 4.3 | 7.4 |
| 6'-Dehydromarmin | 12.1 | 10.3 |
| Geiparvarin | 7.0 | 5.6 |
| (S)—O-Acetylcolumbianetin | 21.7 | 11.6 |

If one experiment was carried out twice or several times the average value was taken.

Example 2

Monoaminooxidase Inhibition by Obliquin

From a stock solution of 0.0405 g of racemic obliquin (92.5%; equal to 37.5 mg of pure compound) in 750 μl of dimethylsulfoxide (DMSO), working solutions were prepared with a concentration of obliquin of $4 \cdot 10^{-4}$ M in reaction buffer (0.05 M sodium phosphate, pH 7.4, 0.2% DMSO). The final concentrations of obliquin in the test system were $10^{-4}$ M, $10^{-5}$ M, $10^{-6}$ M, $10^{-7}$ M.

For determining the inhibition of monoaminoxidases' activity, the Amplex Red Monoamine Oxidase Assay Kit (Molecular Probes Nr._A-12214, Colorimetric version) was conducted according to manufacturers instructions.

As substrates for MAO-A enzyme (Sigma Nr. M7316) p-tyramine and as substrate for MAO-B enzyme (Sigma Nr. M7441) benzylamine were used. The concentration of MAO-A enzyme was 8 Units/ml, and that of MAO-B 4 Units/ml in the working solution.

MAO-A and MAO-B Assay, Colorimetric Version:

For the assay, 50 μl of each working solution (see above) were used. As control solution, the obliquin containing working solution was replaced by 50 μl of the reaction buffer.

50 μl of diluted MAO-A with a final concentration of 2 Units/ml and 50 μl of diluted MAO-B with a final concentration of 1 Unit/ml, respectively, were added.

100 μl of the Amplex solution containing horseradish peroxidase (2 U/ml) and the substrate tyramine (for MAO-A) or the substrate benzylamine (for MAO-B) were added.

To allow a subtraction of the background absorption a mixture of 100 μl of the Amplex solution and 100 μl of the reaction buffer was measured as a "blank".

The samples were incubated at room temperature in the dark for 1 hour, and then the extinction at 535 nm determined in a Softmax Microplate photometer (Molecular Device).

The results are presented in Table 2 and 3.

TABLE 2

Inhibition of MAO-A with increasing concentrations of obliquin.

| Concentration of obliquin [$10^{-7}$ M] | Inhibition of MAO-A [%] |
|---|---|
| 1 | 2.0 |
| 10 | 2.0 |
| 100 | 6.5 |
| 1000 | 24.1 |

TABLE 3

Inhibition of MAO-B with increasing concentrations of obliquin.

| Concentration of obliquin [$10^{-7}$ M] | Inhibition of MAO-B [%] |
|---|---|
| 1 | 8.3 |
| 10 | 33.3 |
| 100 | 76.9 |
| 1000 | 91.5 |

Thus obliquin showed MAO inhibition with a higher specificity for MAO-B than for MAO-A.

Example 3

Porsolt's Swim Test

The "Behavioural Despair Test" or "Porsolt's Forced Swim Test" is a validated animal model for depression (see T. Nagatsu, NeuroToxicology 2004, 25, 11-20, especially p. 16, right column in the middle, in combination with Porsolt et al., Arch. Int. Pharmacodyn. 1977, 229, 327-336). It responds to enhancement of the transmission of several neurotransmitters including serotonine, dopamine and noradrenaline.

The test, which detects antidepressant activity, was carried out as described by Porsolt et al. in Arch. Int. Pharmacodyn. 1977, 229, 327-336. Mice which are forced to swim in a situation from which they cannot escape rapidly become immobile. Antidepressants decrease the duration of immobility.

Mice were individually placed in a cylinder (Height=24 cm, Diameter=13 cm) containing 10 cm water (22° C.) from which they could not escape. The mice were placed in the water for 6 minutes and the duration of immobility during the last 4 minutes was measured.

10 mice were studied per each of the four groups. The test was performed blind, i.e. the person carrying out the experiment was different from the person injecting the mice and didn't thus know to which of the four groups each mouse belonged.

Obliquin was evaluated at 3 doses each: at 10, 30, and 80 mg/kg body weight, administered intraperitonally 30 minutes before the test, and compared with a control group. The thus administered obliquin was dissolved in a saline solution containing 3 weight-% DMSO and 3 weight-% Tween® 80 (so called "vehicle"). To the control group the vehicle consisting of the saline solution containing 3 weight-% DMSO and 3 weight-% Tween® 80 was administered intraperitonally.

Data were analyzed by comparing the treated groups with the control group using the unpaired Student's T tests and Analysis of Variance (ANOVA). They are presented in Table 4.

TABLE 4

Reduction of "immobility time" with increasing concentrations of obliquin.

| Group | Concentration of obliquin [mg/kg body weight] | Duration of immobility [seconds] ± Standard Error of Mean |
|---|---|---|
| Group 1 | 0 (control group) | 176.2 ± 9.4 |
| Group 2 | 10 | 170.4 ± 11.1 |
| Group 3 | 30 | 150.9 ± 9.6 |
| Group 4 | 80 | 132.1 ± 10.5* |

*significantly different (p < 0.01, Student's T test) compared to the control group Thus, with obliquin the immobility time was significantly reduced by 25% in the highest dose group. Overall, there was a significant dose dependent effect of obliquin (ANOVA p<0.05).

Example 4

Marble Burying Test as Test for Anxiety Like or Obsessive Compulsive Behaviour

"Defensive burying" behaviour was demonstrated by rats burying noxious objects, such as drinking spouts filled with a unpleasant-tasting liquid (Wilkie et al., Journal of the Experimental Analysis of Behavior 1979, 31, page 299-306) or shock prods (Pinel and Treit, Journal of Comparative and Physiological Psychology 1978, 92, page 708-712). The marble burying test was devised as a modification of such a test. Poling et al. (Journal of the Experimental Analysis of Behavior 1981, 35, page 31-44) exposed rats to individual cages each containing 25 marbles, daily for 10 or 21 consecutive days. The number of marbles buried, on each day of the 10 d period, or 24 h after the 21 d exposure, were counted. The authors reported that the burying of marbles was not determined by novelty, or due to any noxious stimuli.

Marble burying behaviour by mice is reported to be sensitive to a range of minor (e.g. diazepam) and major (e.g. haloperidol) tranquilisers (Broekkamp et al., Eur J. Pharmacol. 1986, 126, page 223-229), in addition to SSRIs (e.g. fluvoxamine, fluoxetine, citalopram), tricyclic antidepressants (e.g. imipramine, desipramine) and selective noradrenaline uptake inhibitors (e.g. reboxetine), at doses which do not induce sedation. The model may reflect either anxiety-like-or obsessive-compulsive-behaviour (see De Boer and Koolhaas, European Journal of Pharmacology 2003, 463, page 145-161).

The method applied here follows that described by Broekkamp et al. (1986). Mice (n=15 per treatment group) were individually placed in transparent plastic cages (33×21× 18 cm) with 5 cm of sawdust on the floor and 25 marbles (diameter 1 cm) grouped in the centre of the cage. A second, up-turned, cage served as a lid. The number of marbles covered by sawdust (by at least two-thirds) was counted at the end of the 30-minute test period. Tests were performed by investigators blind to the drug treatment protocol.

Prior to testing, all test cages and marbles were "impregnated" by leaving 10 naive mice in each cage for 15 minutes.

7-Geranyl-oxycoumarin was evaluated at 3, 10 and 30 mg/kg, administered i.p. 30 minutes before the test, and compared with a vehicle control group. 7-Geranyl-oxycoumarin was dissolved in a saline solution containing 3 weight-% DMSO and 3 weight-% Tween® 80 (so called "vehicle"). To the control group the vehicle consisting of the saline solution containing 3 weight-% DMSO and 3 weight-% Tween® 80 was administered intraperitonally. Fluoxetine (32 mg/kg), administered under the same experimental conditions, was used as a reference substance.

Data were analysed by comparing treated groups with vehicle control using unpaired Student's t-tests.

Results:

TABLE 5

Effects of 7-geranyl-oxycoumarin and fluoxetine in the marble burying test in mice

| 7-geranyl-oxycoumarin (mg/kg) i.p. −30 minutes | number of marbles covered by sawdust | | |
|---|---|---|---|
| | mean ± s.e.m. | value | % change from control |
| Vehicle | 18.4 ± 1.3 | — | — |
| 3 | 13.4 ± 2.0* | 0.0488 | −27% |
| 10 | 11.3 ± 2.4* | 0.0151 | −39% |
| 30 | 4.7 ± 1.5*** | <0.0001 | −74% |
| fluoxetine: 32 mg/kg i.p. −30 min | 0.3 ± 0.2*** | <0.0001 | −98% | n = 45;
Student's t test:
*= p < 0.05;
***= p < 0.001.

7-Geranyl-oxycoumarin (3, 10 and 30 mg/kg), administered intraperitonally ("i.p.") 30 minutes before the test, dose-dependently decreased the number of marbles covered, as compared with the vehicle control (−27%, p<0.05, −39%, p<0.05 and −74%, p<0.001, respectively).

Fluoxetine (32 mg/kg i.p.), administered under the same experimental conditions, nearly abolished marble burying, as compared with the vehicle control (−98%, p<0.001).

These results show that 7-geranyl-oxycoumarin has a similar activity for reduction in anxiety/obsessive-compulsive behaviour like the SSRI fluoxetine.

Example 5

Preparation of a Soft Gelatin Capsule

A soft gelatin capsule (500 mg) may be prepared comprising the following ingredients:

| Ingredient | Amount per Capsule |
|---|---|
| Obliquin | 200 mg |
| Lecithin | 50 mg |
| Soy bean oil | 250 mg |

Two capsules per day for 3 months may be administered to a human adult for the treatment of mild chronic dysthymia.

Example 6

Preparation of a Soft Gelatin Capsule

A soft gelatin capsule (600 mg) may be prepared comprising the following ingredients:

| Ingredient | Amount per Capsule |
|---|---|
| Obliquin | 200 mg |
| Evening prim rose oil | 300 mg |
| Vitamin $B_6$ | 100 mg |

One capsule per day preferably at the second half of the menstrual cycle may be taken for 14 days for the treatment of premenstrual syndrome and premenstrual dysphoric disorder.

Example 7

Preparation of a Tablet

A 400 mg-tablet may be prepared comprising the following ingredients:

| Ingredient | Amount per tablet |
|---|---|
| Obliquin | 100 mg |
| Passion flower standardized extract | 150 mg |
| Green Tea Extract, e.g. TEAVIGO ® from DSM Nutritional Products, Kaiseraugst, Switzerland | 150 mg |

For general well being, energizing and stress alleviation, one tablet may be taken twice X daily for 3 months.

Example 8

Preparation of an Instant Flavoured Soft Drink

| Ingredient | Amount [g] |
|---|---|
| Obliquin | 0.9 |
| Sucrose, fine powder | 922.7 |
| Ascorbic acid, fine powder | 2.0 |
| Citric acid anhydrous powder | 55.0 |
| Lemon flavour | 8.0 |
| Trisodium citrate anhydrous powder | 6.0 |
| Tricalciumphosphate | 5.0 |
| β-Carotene 1% CWS from DNP AG, Kaiseraugst, Switzerland | 0.4 |
| Total amount | 1000 |

All ingredients are blended and sieved through a 500 μm sieve. The resulting powder is put in an appropriate container and mixed on a turbular blender for at least 20 minutes. For preparing the drink, 125 g of the obtained mixed powder are taken and filled up with water to one liter of beverage.

The ready-to-drink soft drink contains ca. 30 mg Obliquin per serving (250 ml).

As a strenghtener and for general well being 2 servings per day (240 ml) may be drunk.

Example 9

Preparation of a Fortified Non Baked Cereal Bar

| Ingredient | Amount [g] |
|---|---|
| Obliquin | 0.95 |
| Sugar | 114.55 |
| Water | 54.0 |
| Salt | 1.5 |
| Glucose syrup | 130.0 |
| Invert sugar syrup | 95.0 |
| Sorbitol Syrup | 35.0 |
| Palmkernel fat | 60.0 |
| Baking fat | 40.0 |
| Lecithin | 1.5 |
| Hardenend palm-oil | 2.5 |
| Dried and cut apple | 63.0 |
| Cornflakes | 100.0 |
| Rice crispies | 120.0 |
| Wheat crispies | 90.0 |
| Roasted hazelnut | 40.0 |
| Skim milk powder | 45.0 |
| Apple flavour 74863-33 | 2.0 |
| Citric acid | 5.0 |
| Total amount | 1000 |

Obliquin is premixed with skim milk powder and placed in a planetary bowl mixer. Cornflakes and rice crispies are added and the total is mixed gently. Then the dried and cut apples are added. In a first cooking pot sugar, water and salt are mixed in the amounts given above (solution 1). In a second cooking pot glucose, invert and sorbitol syrup are mixed in the amounts given above (solution 2). A mixture of baking fat, palmkernel fat, lecithin and emulsifier is the fat phase. Solution 1 is heated to 110° C. Solution 2 is heated to 113° C. and then cooled in a cold water bath. Afterwards solution 1 and 2 are combined. The fat phase is, melted at 75° C. in a water bath. The fat phase is added to the combined mixture of solution 1 and 2. Apple flavour and citric acid are added to the liquid sugar-fat mix. The liquid mass is added to the dry ingredients and mixed well in the planetary bowl mixer. The mass is put on a marble plate and rolled to the desired thickness. The mass is cooled down to room temperature and cut into pieces. The non baked cereal bar contains ca. 25 mg obliquin per serving (30 g). For general well-being and energizing 1-2 cereal bars may be eaten per day.

The invention claimed is:

1. A method of maintaining a balanced cognitive function, helping to reduce the risk of mood swings, helping to retain a positive mood and supporting cognitive wellness comprising:
administering to an animal, including a human, an effective amount of a dietary or pharmaceutical composition comprising a compound selected from the group consisting of: obliquin and auropten and the compound of Formula VII:

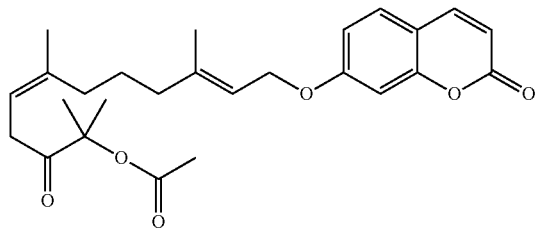

VII and observing a balanced cognitive function, reduced mood swings, retention of a positive mood or cognitive wellness.

2. A method according to claim 1 wherein the composition is a food, feed or dietary supplement.

3. A method according to claim 1 wherein the individual is a non-human animal.

4. A method according to claim 1 wherein the effective amount is 1 mg to 500 mg per dosage unit.

5. A method according to claim 1 wherein the dietary composition is a food or beverage and the effective amount is 100/kg to 5 g/kg, based on the total weight of the food or beverage.

* * * * *